US006423534B1

(12) United States Patent
Shiba et al.

(10) Patent No.: US 6,423,534 B1
(45) Date of Patent: Jul. 23, 2002

(54) METHOD FOR ELIMINATING ETHANOL IN EXHAUST GAS

(75) Inventors: Hirotaka Shiba, Osaka; Chieko Tada; Takeshi Saeki, both of Hyogo; Nobuya Matsumoto, Osaka, all of (JP)

(73) Assignee: Suntory Limited, Osaka (JP)

( * ) Notice: Subject to any disclaimer, the term of this patent is extended or adjusted under 35 U.S.C. 154(b) by 0 days.

(21) Appl. No.: 09/403,489

(22) PCT Filed: Feb. 23, 1999

(86) PCT No.: PCT/JP99/00797

§ 371 (c)(1),
(2), (4) Date: Oct. 22, 1999

(87) PCT Pub. No.: WO99/42563

PCT Pub. Date: Aug. 26, 1999

(30) Foreign Application Priority Data

Feb. 23, 1998 (JP) ............................................ 10-040253

(51) Int. Cl.[7] .................................................. C12S 5/00
(52) U.S. Cl. ....................................... 435/266; 435/262
(58) Field of Search ............................. 435/262, 262.5, 435/266, 299.1

(56) References Cited

U.S. PATENT DOCUMENTS

| 3,645,846 | A | * | 2/1972 | Imada et al. |
| 3,929,578 | A | | 12/1975 | Urakami |
| 4,421,534 | A | * | 12/1983 | Walker |
| 4,662,900 | A | * | 5/1987 | Ottengraf |
| 5,116,505 | A | * | 5/1992 | Lourens et al. |
| 5,521,131 | A | * | 5/1996 | Higa |

FOREIGN PATENT DOCUMENTS

| DE | 37 05 837 | * | 6/1988 |
| DE | 195 26 788 C1 | * | 11/1996 |
| JP | 53-28984 | | 8/1978 |
| JP | 2-293016 | | 12/1990 |

OTHER PUBLICATIONS

Bijl. Caplus Abstract No. 1988:26450 of Neth. Environ. Technol., Proc. Eur. Conf., 2nd (1987), 358–60*
Jol et al. Caplus Abstract No. 1990:144824 of Dechema Biotech. Conf. (1988), pp. 373–389.*
Shim et al. Caplus Abstract No. 1995:817765 of J. Chem. Technol Biotechnol. (1995), vol. 65, No. 1, pp. 49–54.*
Shim et al., Oxidation of Ethanol Vapors in a Spiral Bioreactor. J. Chem. Tech. Biotechnol., (1995) vol. 65, No. 1, pp. 49–54.

* cited by examiner

*Primary Examiner*—William H. Beisner
(74) *Attorney, Agent, or Firm*—Paul E. White, Jr.; Manelli Denison & Selter PLLC

(57) ABSTRACT

A method and an apparatus for decomposing and eliminating ethanol in an exhaust gas by bringing the ethanol in the exhaust gas into contact with an ethanol-utilizing microorganism held in a filter bed are provided. A microorganism selected from the genus Candida, the genus Pichia and/or the genus Hansenula is used as the ethanol-utilizing microorganism, whereby a method and an apparatus having a high removal efficiency of ethanol in the exhaust gas, and being capable of long-term, stable decomposition and elimination of ethanol under high concentration, high load capacity, can be provided.

10 Claims, 5 Drawing Sheets

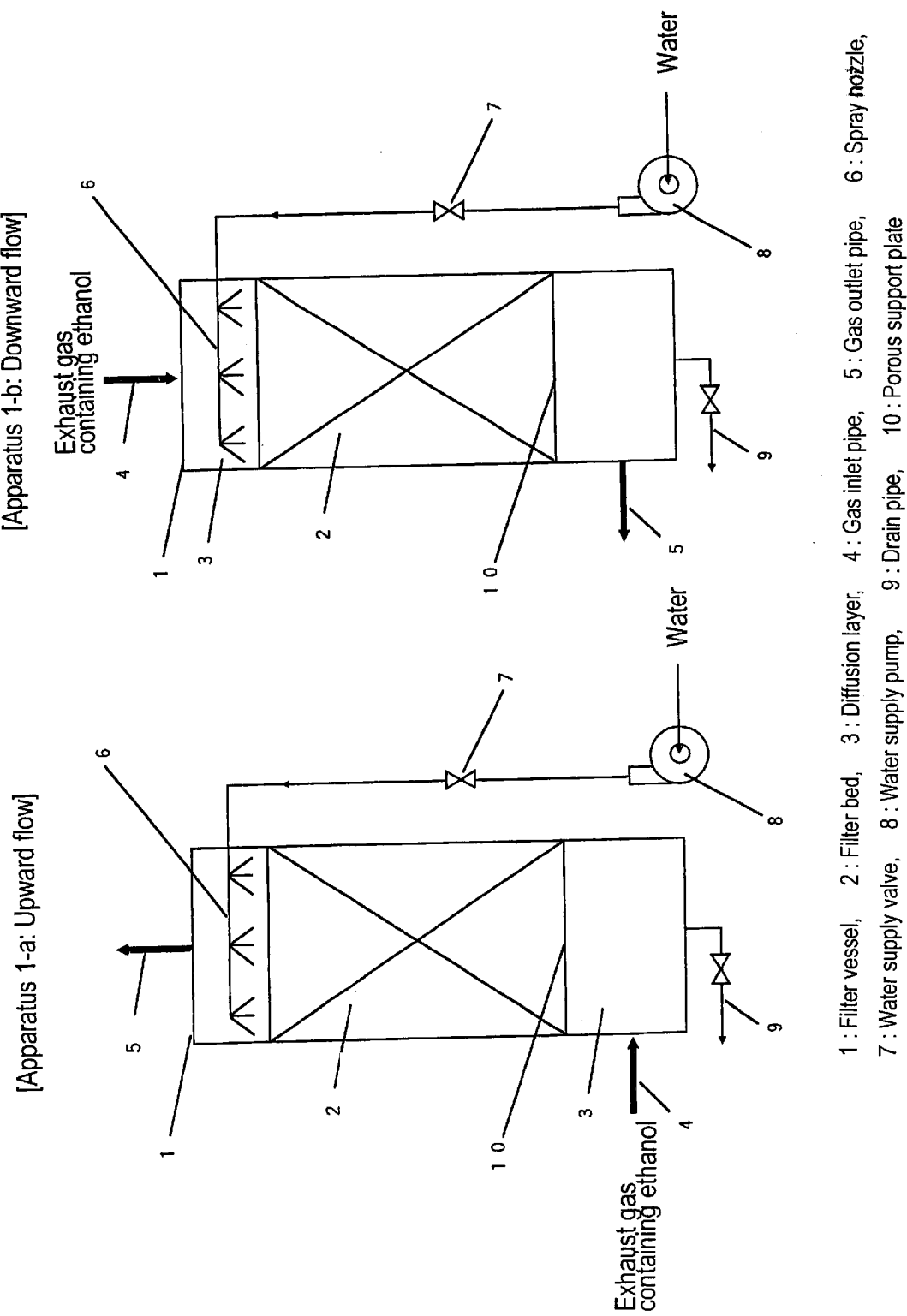

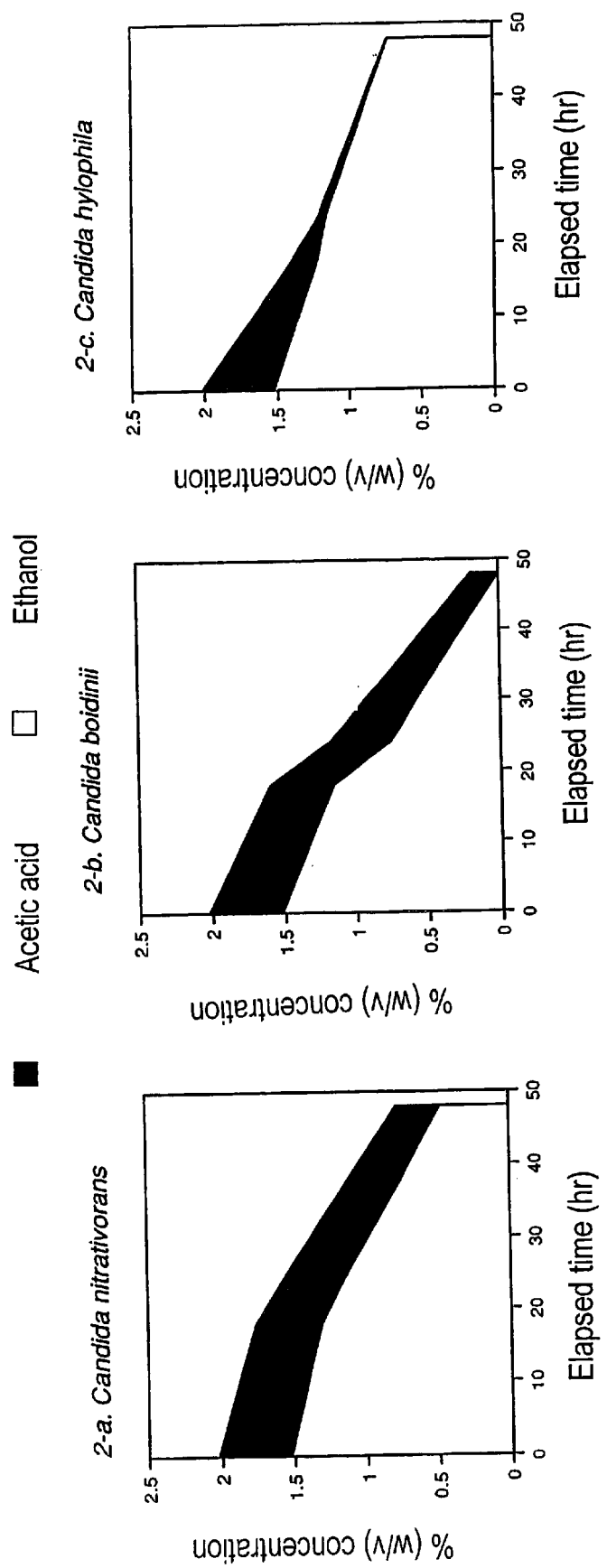
Fig. 2 Comparisons of acetic acid utilizing ability of microorganisms in the presence of ethanol

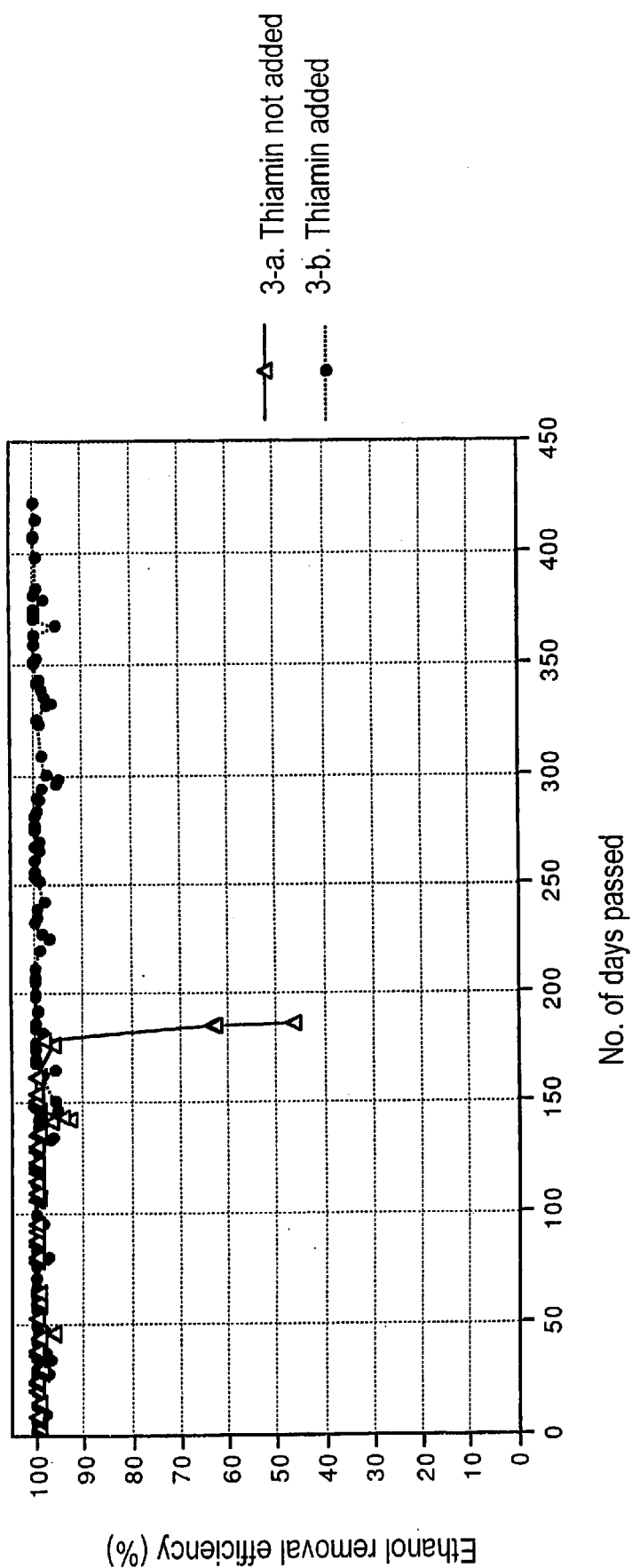
Fig. 3 Time courses of ethanol removal efficiency with and without addition of thiamin (ethanol load capacity: 120 g ethanol/m³ filter bed/hr)

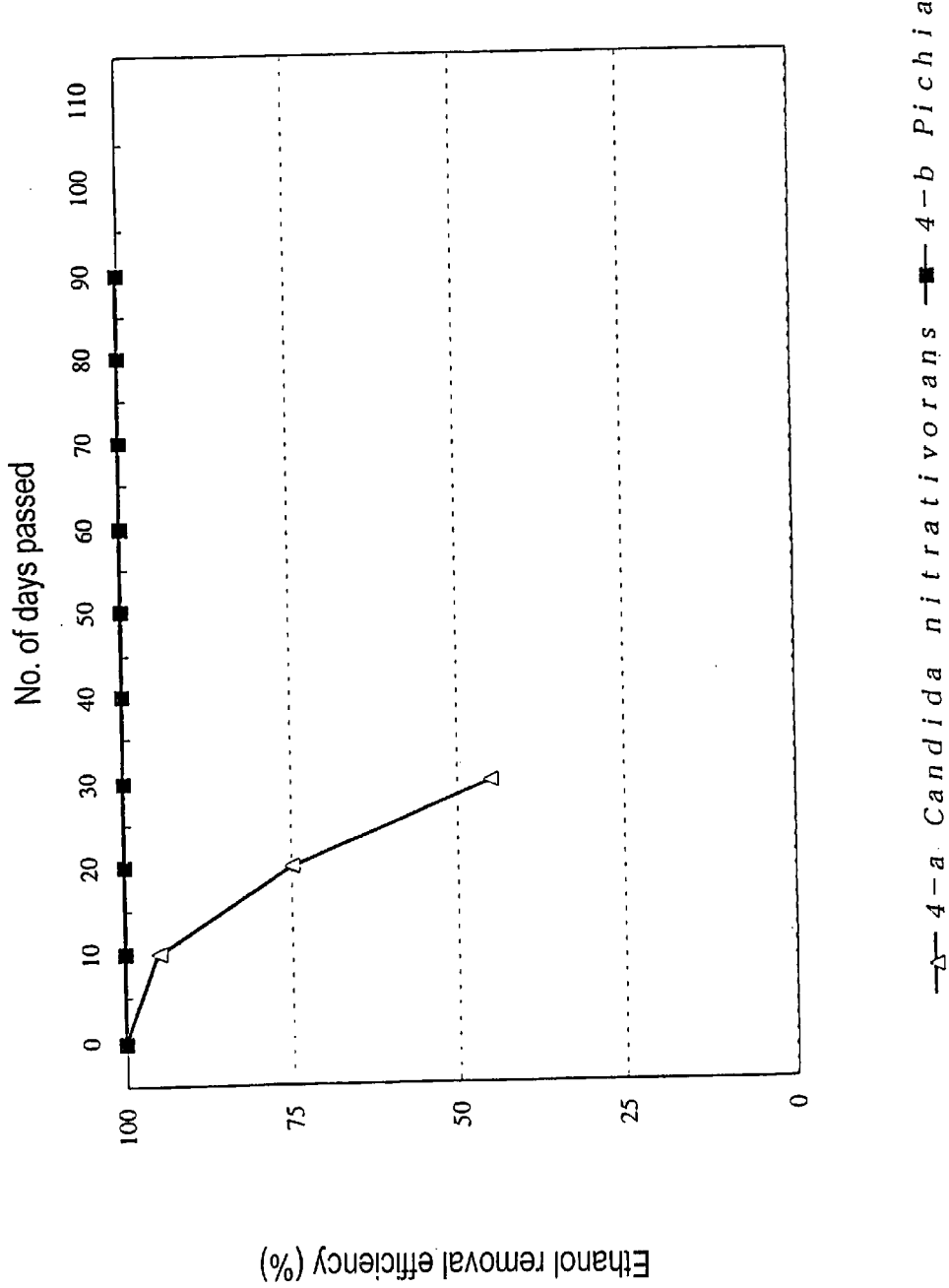
Fig. 4 Time course of ethanol removal efficiency by ethanol-utilizing microorganism resistant to high temperature (ethanol load capacity: 120 g ethanol/m³ filter bed/hr, test atmosphere temperature 37°C)

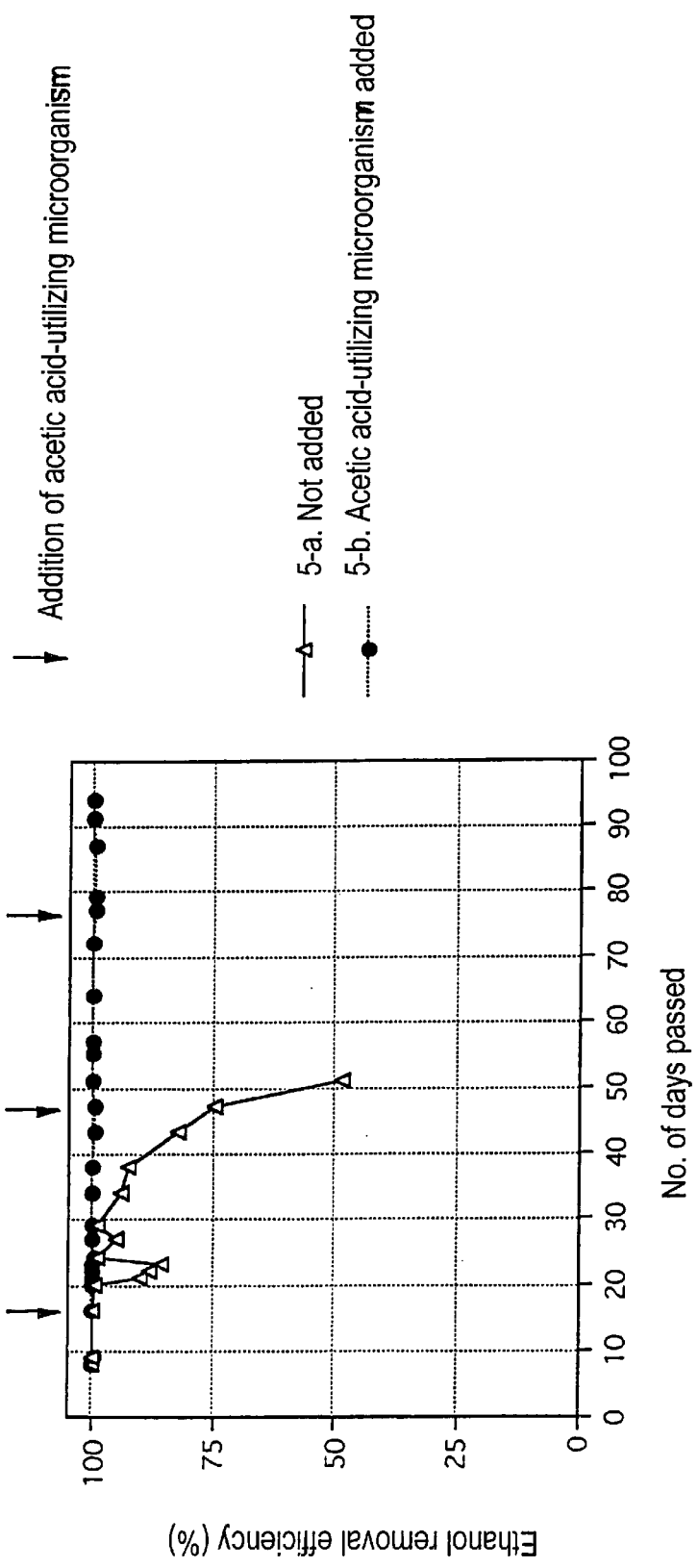

METHOD FOR ELIMINATING ETHANOL IN EXHAUST GAS

This application is the national phase of international application PCT/JP99/00797 filed Feb. 23, 1999 which designated the U.S.

TECHNICAL FIELD

This invention relates to a novel method for eliminating ethanol in an exhaust gas by use of a microorganism. More specifically, the invention relates to a method for eliminating ethanol, comprising passing an exhaust gas, which contains ethanol, etc., through a filter bed holding an ethanol-utilizing microorganism, to bring the ethanol, etc. into contact with the microorganism, thereby decomposing the ethanol, etc. so that the ethanol, etc. may be directly eliminated from the exhaust gas. The invention also relates to an apparatus used in performing this method.

BACKGROUND ART

Ethanol is one of the volatile organic compounds which contributes to the destruction of the ozone layer, although not to such a high degree as methane. Thus, it is necessary to suppress the emission of ethanol-containing exhaust gases formed during the manufacturing process for fermentation products, for example, at bakery, soy sauce plants, alcohol production plants, and breweries or distilleries; or those generated, for example, at laundry factories using ethanol as a solvent. This is a crucial task for the protection of the earth's environment.

Exhaust gas containing ethanol have often been eliminated by methods, such as flame incineration using a boiler or the like, catalytic combustion, adsorption to activated carbon or resin, and dissolution into water by mans of a scrubber or by cooling condensation. Treating methods other than burning have required that ethanol be recovered, and then further subjected to combustion or microbial treatment as a post-recovery step.

These methods, however, have been seriously problematical in terms of strict requirements for the site of construction of facilities generating ethanol-containing exhaust gas; restrictions on options for eliminating methods, due to limited use of utilities (electricity, water, drainage); huge initial investments, and high running costs; huge equipment and land allotments for installation. Furthermore, none of these methods have fulfilled all of the requirements regarding treatment ability, economy, safety, as well as ease of maintenance and management.

Methods for eliminating or decomposing substances by use of microorganisms have been developed for sewage disposal, waste water treatment, environmental repair, e.g., through decomposition of effluent oils into seawater, removal of environmental foul odors, and so on. A bioscrubber, which circulates activated sludge water with a scrubber, is known as a device for directly decomposing and removing ethanol in an exhaust gas by use of a microorganism. However, this bioscrubber device treats ethanol, dissolved in activated sludge water, by means of activated sludge in a huge aeration tank mounted in succession to the scrubber. Introduction of this device has required huge equipment and a significant investment.

Another device for eliminating exhaust by use of a microorganism is a biofilter. The biofilter is a device in which an exhaust gas to be treated is passed through a microorganism immobilized in a filter material, so that a target substance is treated by the action of the microorganism in the filter bed. The advantage of this device is that it is more compact and lower in running costs than ordinary activated sludge treatment. However, the existing biofilter has been effective only when the concentration of the target substance to be treated, which is contained in the exhaust gas, is as low as, say, several hundred ppm or less. Such a biofilter with a limited power has been commercially unfeasible.

The method for elimination or decomposition using a microorganism has posed problems, such that it cannot be performed continuously for a long term, it lacks a stable treating ability, and the apparatus involved has complicated maintenance requirements.

Some reports have been issued on the existing techniques for the biofilter that decomposes or eliminates ethanol contained in an exhaust gas. The main information from the reports is offered below.

In the present specification, the ethanol load capacity refers to the amount (weight) of ethanol introduced into the biofilter device per unit time and per unit volume of the filter bed. The ethanol removal efficiency is the rate (percentage) of {[the amount of ethanol (absolute amount) introduced into the biofilter device] minus [the amount of ethanol (absolute amount) in the exhaust gas after discharge from the biofilter device]} to [the amount of ethanol (absolute amount) introduced into the biofilter device].

Hodge et al. reported a test conducted on a small scale, i.e., a laboratory scale (D. S. Hodge and J. S. Devinny, Environmental Progress, Vol. 13, 167–173 (1994)). A cylindrical column with a volume of 4 liters (7.6 cm in diameter by 90 cm in length) was charged with activated carbon as a filter material, and soil from a petroleum refinery land firm was used as a source of a microorganism. When a gas was passed at an ethanol load capacity of 71 to 245 $g/m^3/hr$, the ethanol removal efficiency was 72 to 89%. However, the test results were not confirmed for a long-term continuous operation.

Kiared et al. also reported a test conducted on a small scale, i.e., a laboratory scale (K. Kiared, L. Bibeau, R. Brzeinski, Environmental Progress, Vol. 15, 148–152 (1996)). A cylindrical column with a volume of 21 liters (15 cm in diameter by 120 cm in length) was charged with peat as a filter material, and a mixture of Bacillus was used as a source of a microorganism. When a gas was passed at an ethanol load capacity of 135 $g/m^3/hr$, the ethanol removal efficiency was 88%. However, these results were obtained in a continuous operation performed for up to 30 days.

As large scale, i.e., plant scale, experiments, pilot experiments for elimination of exhaust gas at a bakery have been reported (G. Leson et al., Proceedings of the 86th Annual Meeting of Air & Waste association, 93-WP-52C. 04, pp. 1–14 (1993)). Compost was used as a microorganism source in a reactor with a capacity of 1.42 $m^3$ (1 m in diameter by 1.83 m in height with 2 layers arranged in series). This device was operated, with a gas being passed as a downward flow. At load capacities of 70 $g/m^3/hr$ or less, the ethanol removal efficiency was 100%. At load capacities in excess of 100 $g/m^3/hr$, the ethanol removal efficiencies were less than 90%. When the load capacities were 300 $g/m^3/hr$ or more, the ethanol removal efficiencies were reported to be 50% or less. These results were also obtained in a continuous operation lasting for a short term of less than 2 months.

Leson et al. similarly reported testing of a full-scale biofilter for elimination of exhaust gas containing ethanol (G. Leson et al., Proceedings of the 88th Annual Meeting of Air & Waste association, 95-WP-9A. 04, pp. 1–11 (1995)).

They conducted experiments for treating a foundry exhaust gas, which contained ethanol at a flow rate of 17,000 m$^3$/hr, by a biofilter device with a filter bed volume of 280 m$^3$. In these experiments, a mixture of wood chips, agricultural waste, and manure was used as a filter material.

The treating ability in the initial stage of operation was reported to be the ethanol removal efficiency of 80 to 90% on an average of an ethanol load capacity of 100 to 180 g/m$^3$/hr. No report of long-term operation was made, so that the results of long-term operation, with a constantly high ethanol removal efficiency being maintained stably, are unknown.

Shim et al. reported a test of ethanol decomposition using a spiral type bioreactor having activated sludge immobilized therein (J. S. Shim et al., J. Chem. Tech. Biotechnol., Vol. 64, 49–54(1995)). They reported that 99% ethanol was removed from an exhaust gas containing 7,000 ppm ethanol at a maximum load capacity of 185 g/m$^3$/hr (unit reactor volume). However, they did not carry out a long-term operation test.

Except for the report by Shim et al., all the reports showing the ethanol removal efficiency of 90% or more are concerned with the treatment of an exhaust gas having a low concentration of ethanol as indicated by the ethanol load capacity of 100 to 180 g/m$^3$/hr. Further these reports did not include the results of operation performed continuously for a long term of 3 months or more. That is, there has been no development of a biofilter for decomposition or elimination of ethanol in an exhaust gas, the biofilter that ensures sufficient decomposition or elimination at a high ethanol load capacity of 180 g/m$^3$/hr or more, that permits a long-term continuous operation with this treating ability being maintained, and that can be put to practical use on a plant scale.

Under these circumstances, the inventors of the present invention accomplished a novel method for eliminating ethanol in an exhaust gas by use of a microorganism, as means of decomposing an ethanol-containing exhaust gas formed during the manufacturing process for fermentation products, for example, at bakery, soy sauce plants, alcohol production plants, and breweries or distilleries; or generated, for example, at laundry factories using ethanol as a solvent. The novel method is low in running costs, obviates the need for devices or equipment requiring a heavy initial investment, is more convenient in device maintenance, is easy to handle, can be continuously performed for a long term of more than a half year, is able to decompose ethanol in an exhaust gas having a high concentration of ethanol and a high load capacity, and is high in ethanol removal efficiency, and elimination can be performed at a high speed.

DISCLOSURE OF THE INVENTION

The method of the present invention comprises passing an ethanol-containing exhaust gas through an ethanol-utilizing microorganism held in a filter bed, to bring the ethanol into contact with the microorganism, thereby decomposing the ethanol in the exhaust gas directly by the microorganism. This method permits rapid elimination of ethanol. The present invention also provides a eliminating method which can decompose acetaldehyde, ethyl acetate, and acetic acid, along with ethanol, by the microorganism, even when the exhaust gas contains acetaldehyde, ethyl acetate, and/or acetic acid, in addition to ethanol.

BRIEF DESCRIPTION OF THE DRAWINGS

FIGS. 1-a and 1-b are views showing examples of an apparatus according to the present invention;

FIGS. 2-a, 2-b, and 2-c are graphs showing the time courses of ethanol utilization and acetic acid utilization of three strains, *Candida hylophila, Candida nitrativorans*, and *Candida boidinii* selected in Experimental Examples 1 and FIG. 3 is a graph showing the time courses of the ethanol removal efficiency in the presence and absence of thiamin in an ethanol eliminating method according to the present invention;

FIG. 4 is a graph showing the time course of the ethanol removal efficiency of a high temperature resistant, ethanol-utilizing microorganism; and FIG. 5 is a graph showing the time courses of the ethanol removal efficiency according to the co-presence or absence of a microorganism capable of utilizing acetic acid in the presence of ethanol in the ethanol eliminating method of the invention.

BEST MODE FOR CARRYING OUT THE INVENTION

The present invention provides a method for eliminating ethanol by use of an ethanol-utilizing microorganism, and further provides a method for eliminating ethanol by the joint use of an ethanol-utilizing microorganism, and a microorganism capable of utilizing acetic acid in the presence of ethanol. The present invention also provides a method for eliminating ethanol, which is higher in eliminating speed and permits a long-term continuous operation, by supplying thiamin or a thiamin-containing substance to the microorganism.

As the ethanol-utilizing microorganism in the present invention, a microorganism selected from the genus Candida, the genus Pichia and/or the genus Hansenula, for example, is preferably used.

Among the genus Candida, preferred examples are microorganisms of *Candida nitrativorans*, such as ATCC 22941; microorganisms of *Candida boidinii*, such as IFO 10035, ATCC 96315, ATCC 44637, ATCC 62807, ATCC 90439, ATCC 32929, ATCC 90411, ATCC 36351, ATCC 38256, ATCC 38257, ATCC 60364, ATCC 46498, ATCC 96926, ATCC 56507, ATCC 20432, ATCC 56897, ATCC 23175, and ATCC 56294; microorganisms of *Candida krusei*, such as IFO 0011, ATCC 749, IFO 1064, ATCC 2340, ATCC 38293, ATCC 32672, ATCC 32545, ATCC 62403, ATCC 62404, ATCC 64675, ATCC 34135, ATCC 20298, ATCC 34077, ATCC 2159, ATCC 14243, ATCC 200339, ATCC 200554, ATCC 36353, and ATCC 44057; microorganisms of *Candida lambica*, such as ATCC 24750; microorganisms of *Candida kefyr*, such as IFO 0886; microorganisms of *Candida sake*, such as IFO 1021; and microorganisms of *Candida solani*, such as ATCC 14440.

Among the genus Pichia, preferred examples are microorganisms of *Pichia anomala*, such as JCM 3538, IFO 0140, IFO 0127, ATCC 4103, ATCC 18205, ATCC 2349, ATCC 8202, ATCC 8167, ATCC 2581, ATCC 580, ATCC 4104, ATCC 46058, ATCC 60231, ATCC 8170, ATCC 18860, ATCC 60811, ATCC 58044, ATCC 20257, ATCC 46131, and ATCC 34080; microorganisms of *Pichia rhodanensis*, such as ATCC 24191; and microorganisms of *Pichia angusta*, such as ATCC 64209.

Among the genus Hansenula, preferred examples are microorganisms of *Hansenula anomala*, such as IAM 4967, ATCC 2149, and ATCC 8168, or microorganisms of *Hansenula panis*, all currently classified as *Pichia anomala*; and microorganisms of *Hansenula sydowiorum*, such as ATCC 58369, currently classified as *Pichia sydowiorum*.

Furthermore, acetaldehyde, ethyl acetate and/or acetic acid usually incorporated in the exhaust gas containing ethanol can also be decomposed by the microorganism disclosed in the present invention, as can ethanol.

As the microorganism used in the invention, which is capable of utilizing acetic acid in the presence of ethanol, a microorganism selected from among the genus Candida is preferably used. Among the genus Candida, *Candida hylophila*, such as ATCC 22875, is particularly preferred.

The method of bringing the ethanol-utilizing microorganism of the present invention into contact with ethanol in the exhaust gas involves providing a packed tank having the microorganism carried on a filter material, and passing the exhaust gas containing ethanol through the filter bed to bring the ethanol-containing exhaust gas into contact with the microorganism in the filter bed. As the filter material for carrying this microorganism, the present invention can use any of peat moss, vermiculite, zeolite, pearlite, ion exchange resin, compost, soil, diatomaceous earth, sawdust, wood chips, powdered waste paper, cellulose powder, pumice, activated carbon, charcoal, urethane, PVA resin, and metal slug.

To operate the apparatus of the invention stably, it is particularly preferred that the microorganism be added, for example, in an amount of 104 cells/ml to 1010 cells/ml in the filter bed. However, the concentration of the microorganism can be selected arbitrarily depending on the concentration of ethanol in the exhaust gas, the amount of loading of the exhaust gas, the flow rate of the exhaust gas, etc.

Water necessary for the growth of the microorganism is fed, where necessary, to the filter bed by such means as a shower nozzle.

The path of a decomposition reaction of ethanol is such that ethanol is decomposed into acetaldehyde, the acetaldehyde is decomposed into acetic acid, and the acetic acid is converted into acetyl-CoA, which is decomposed via the TCA cycle. The inventors aimed at further promoting the decomposition of ethanol by activating this TCA cycle. With this background, they conducted extensive studies on the effects of supply of various substances to microorganisms. As a result, they found that the decomposition of ethanol can take place more easily, and can be performed at a high speed, by supplying the microorganism with thiamin which is utilized in the TCA cycle, or a substance containing thiamin. The present invention provides a method for eliminating ethanol in an exhaust gas more rapidly and stably, by adding thiamin or a substance containing thiamin into the filter bed.

The thiamin or thiamin-containing substance used in this invention includes, for example, thiamin hydrochloride, etc. as thiamin itself, and thiamin-containing materials including cereals such as rice bran and wheat germ, the germ part of cereals, beans such as soybean, seeds of plants such as sesame and sunflower, seaweed, meat and its processed products, and complex nutrients such as yeast extract and malt extract. Any of these substances can be used similarly in the present invention.

The thiamin or thiamin-containing substance can be fed to the microorganism by adding it to the filter bed holding the microorganism. The addition of the thiamin or thiamin-containing substance to the filter bed can be carried out, for example, by directly mixing thiamin or thiamin-containing substance to the filter bed, or by forming the thiamin or thiamin-containing substance into an aqueous solution or suspension, and sprinkling the solution or suspension over the filter bed by use of a sprinkling line.

The amount of the thiamin or thiamin-containing substance added to the filter bed may be 1 $\mu$g or more as thiamin per liter of the filter bed, and the amount of 50 to 200 $\mu$g per liter of the filter bed is used more preferably. If the substance containing thiamin is rice bran, for example, its amount is 2 g or more per liter of the filter bed.

The thiamin or thiamin-containing substance may be added to the filter bed at any time, such as at the start of the ethanol eliminating method, or during the execution of the ethanol eliminating method.

When ethanol is decomposed, acetaldehyde, ethyl acetate and/or acetic acid, the intermediate products during its decomposition process, may accumulate in the filter bed holding the microorganism. Particularly under high ethanol load capacity, accumulation of these intermediate products can occur easily. If the accumulation of acetic acid, in particular, among these intermediate products becomes excessive, the pH in the filter bed may also be affected, and the ethanol utilizing ability of the microorganism becomes easily suppressed. Consequently, its ethanol utilizing ability may decline, or the proliferation and growth of the microorganism may be inhibited. Under these situations, the inventors have found that the decomposition of ethanol can be performed stably and at a high speed, by using the microorganism capable of utilizing acetic acid in the presence of ethanol, along with the ethanol-utilizing microorganism, as the microorganism to be brought into contact with ethanol.

When the method for eliminating ethanol according to the present invention is performed at a high speed, or under conditions involving a high load of ethanol in the exhaust gas, the carbon source (C)/nitrogen source (N) ratio in the filter bed tends to be shifted considerably toward the carbon (C) side. For full growth of the microorganism, therefore, it is preferred to add a nitrogen source (N). As the nitrogen source, an ammonium salt or a nitrate, such as ammonium nitrate, ammonium chloride, ammonium sulfate or sodium nitrate, ammonia, urea, amines, amino acid or yeast extract or other complex substances may be used arbitrarily. For the full growth of the microorganism, not only the nitrogen source, but a phosphorus source is preferably added. As the phosphorus source, a phosphate such as dipotassium hydrogenphosphate or disodium hydrogenphosphate, or a complex substance such as yeast extract may be used arbitrarily. Furthermore, when the pH in the filter bed markedly changes at the start of, or during, the ethanol eliminating method, the addition of a pH adjustor is preferred to lessen stress on the microorganism. The pH adjustor may be, but not restricted to, calcium carbonate, calcium hydroxide, or sodium hydroxide. Such treatment, for example, can result in the proper growth of the microorganism.

An example of the apparatus according to the present invention is shown below. As illustrated in FIGS. 1-*a* and 1-*b*, a filter bed 2 is provided with a porous support plate at its bottom. The inside of the filter bed 2 is packed with a filter material, and a microorganism is carried in the filter bed. Above the filter bed 2, a spray nozzle 6 is provided. The spray nozzle 6 is connected to a water supply pump 8 via a water supply valve 7 so as to spray water onto the filter bed 2, when necessary. With the apparatus shown in FIG. 1-*a*, a diffusion layer 3 is provided below the filter bed 2. With the apparatus shown in FIG. 1-*b*, a diffusion layer 3 is provided above the filter bed 2. Since an exhaust gas stagnates in the diffusion layer 3, the exhaust gas can be introduced uniformly into the filter bed 2. At a lower part of the apparatus, a drain pipe 9 is provided so that drainage accumulated in a lower part of the filter bed can be discharged to the outside of the apparatus, where necessary. In FIG. 1-*a*, an exhaust gas containing ethanol is passed through the filter bed 2 upward from below the filter bed 2. In FIG. 1-*b*, an exhaust gas containing ethanol is passed through the filter bed 2 downward from above the filter bed 2. In each of both types of the apparatus, the microorganism in the filter bed 2 and the ethanol-containing exhaust gas passed through the filter bed 2 are brought into contact to decompose ethanol. The exhaust gas with the ethanol removed is discharged through a gas outlet pipe 5.

The present invention will be described in more detail by way of the following Experimental Examples and Examples for working of the invention.

EXPERIMENTAL EXAMPLE 1

Selection of ethanol-utilizing microorganisms

The following microorganisms were checked for the ability to utilize ethanol:

Microorganisms Used in the Test

*Brettanomyces anomalus* ATCC 10599
  *Brettanomyces bruxellensisi* IFO 0677
  *Brettanomyces claussenii* ATCC 10562
  *Brettanomyces lambicus* ATCC 10563
  *Candida aaseri* ATCC 18805
  *Candida boidinii* CTW (isolated strain)
  *Candida cantarellii* IFO 10269
  *Candida hylophila* CR30 (isolated strain)
  *Candida lambica* ATCC 24750
  *Candida kefyr* IFO 0886
  *Candida krusei* IFO 0011
  *Candida krusei* ATCC 749
  *Candida melibiosica* IFO 10401
  *Candida mesenterica* JCM 7531
  *Candida mesenterica* ATCC 10569
  *Candida nitrativorans* CY 4–1G (isolated strain)
  *Candida sake* IFO 1021
  *Candida solani* ATCC 14440
  *Candida vinaria* ATCC 24745
  *Candida vini* ATCC 18823
  *Cryptococcus humicolus* ATCC 14438
  *Hansenula anomala* IAM 4967
  *Hansenula anomala* ATCC 2149
  *Hansenula anomala* ATCC 8168
  *Hasegawaea japonica* ATCC 10660
  *Pichia angusta* ATCC 14754
  *Pichia angusta* ATCC 64209
  *Pichia anomala* JCM 3538
  *Pichia anomala* IFO 0127
  *Pichia anomala* IFO 0140
  *Pichia rhodanensis* ATCC 24191
  *Rhodotorula javanica* ATCC 24010

All the isolated strains were isolated from the surface layer of the soil.

Composition of Culture Medium for Testing of Ethanol Utilizing Ability

| Basal medium | |
| --- | --- |
| $(NH_4)_2HPO_4$ | 5 g |
| $(NH_4)_2SO_4$ | 4 g |
| $KH_2PO_4$ | 2 g |
| $MgSO_4 \cdot 7H_2O$ | 0.5 g |
| Yeast extract | 0.1 g |
| $FeSO_4 \cdot 7H_2O$ | 35 mg |
| $MnSO_4 \cdot 5H_2O$ | 8.8 mg |
| Water | 1 liter |
| pH 6.2 | |
| Ethanol | |
| Ethanol | 20 ml |

The basal medium was autoclaved at 121° C. for 15 minutes, and then ethanol was added thereto to form a culture medium for testing.

Method for Preincubation of Test Microorganism

An 80 ml test tube was charged with 10 ml of a liquid medium of the composition: 21 g Bacto YM Broth (a product of Difco containing 3 g yeast extract, 3 g malt extract, 5 g peptone, and 10 g dextrose) per liter of water. The test microorganism was cultured for 24 to 48 hours in the test tube, and the resulting culture was used as a liquid culture of the test microorganism.

Testing Method

To an 80 ml test tube containing 10 ml of the basal medium for ethanol utilizing ability testing, 0.2 ml of ethanol was added, and 0.2 ml of the liquid inoculum culture of the test microorganism was further added. The mixture was shake cultured (300 rpm) at 30° C. for 48 to 96 hours by means of a reciprocating shaker. The time course of the ethanol concentration in the inoculum culture during culture was measured by high performance liquid chromatographic analysis at intervals of 24 hours during the culturing period. The HPLC analysis was made using a column Aminex HPX-87H (8 mm$\phi$×300 mm, Bio-Rad), a mobile phase of 0.01 N sulfuric acid, a flow rate of 0.6 ml/min, at room temperature, and a differential refractometer for detection. Based on the time course of the decrease in the ethanol concentration in the inoculum culture, the test microorganisms that were able to decompose 0.3% (w/v) or more of ethanol in 24 hours were selected as the microorganisms with high ethanol utilizing ability. The following microorganisms were selected:

Selected Microorganisms with High Ethanol Utilizing Ability

*Candida boidinii* CTW (isolated strain)
  *Candida hylophila* CR30 (isolated strain)
  *Candida lambica* ATCC 24750
  *Candida kefyr* IFO 0886
  *Candida krusei* IFO 0011
  *Candida krusei* ATCC 749
  *Candida nitrativorans* CY 4-IG (isolated strain)
  *Candida sake* IFO 1021
  *Candida solani* ATCC 14440
  *Hansenula anomala* IAM 4967
  *Hansenula anomala* ATCC 2149
  *Hansenula anomala* ATCC 8168
  *Pichia anomala* JCM 3538
  *Pichia anomala* IFO 0140
  *Pichia angusta* ATCC 64209
  *Pichia rhodanensis* ATCC 24191

EXPERIMENTAL EXAMPLE 2

Selection of microorganism capable of utilizing acetic acid in the presence of ethanol.

The microorganisms used in Experimental Example 1 were checked for the ability to utilize acetic acid in the presence of ethanol.

[Culture Medium for Evaluation of Acetic Acid Utilizing Ability in the Presence of Ethanol]

| Basal medium | |
|---|---|
| $K_2HPO_4$ | 3 g |
| $Na_2HPO_4 \cdot 12H_2O$ | 6 g |
| NaCl | 15 g |
| $NH_4Cl$ | 1 g |
| $MgSO_4 \cdot 7H_2O$ | 0.246 g |
| Vitamin $B_1$ hydrochloride | 4 mg |
| Acetic acid | 5 ml |
| $FeSO_4 \cdot 7H_2O$ | 35 mg |
| $MnSO_4 \cdot 5H_2O$ | 8.8 mg |
| Water | 1 liter |
| pH 6.0 | |
| Ethanol | |
| Ethanol | 20 ml |

The basal medium was autoclaved at 121° C. for 15 minutes, and then ethanol was added thereto for use as a culture medium for evaluation.

The preincubation of each test microorganism was performed in the same manner as in Experimental Example 1 to obtain a liquid culture of the test microorganism.

Testing Method

To an 80 ml test tube containing 10 ml of the basal medium for testing of acetic acid utilizing ability in the presence of ethanol, 0.2 ml of ethanol was added, and 0.2 ml of the liquid culture of the test microorganism was further added. The mixture was shake cultured (300 rpm) at 30° C. for 48 to 72 hours by means of a reciprocating shaker. The time courses of the ethanol concentration and the acetic acid concentration in the inoculum culture during culture were measured by high performance liquid chromatographic analysis at intervals of 24 hours. The HPLC analysis was made using a column Aminex HPX-87H (8 mm$\phi$×300 mm, Bio-Rad), a mobile phase of 0.01 N sulfuric acid, a flow rate of 0.6 ml/min, at room temperature, and a differential refractometer for detection. Based on the time course of the decrease in the acetic acid concentration in the inoculum culture, the test microorganism that was able to decompose 0.4% (w/v) or more of acetic acid in 24 hours was selected as the microorganism with acetic acid utilizing ability in the presence of ethanol. The following microorganism was selected:

Selected Microorganism with Acetic Acid Utilizing Ability in the Presence of Ethanol

*Candida hylophila* CR30 (isolated strain)

FIGS. 2-*a*, 2-*b*, and 2-*c* show the time courses of the ethanol concentration and the acetic acid concentration in the inoculum culture for three strains, i.e., the selected strain *Candida hylophila* CR 30, and two strains with high ethanol decomposing ability, *Candida nitrativorans* CY 4-IG and *Candida boidinii* CTW. In the graphs, the horizontal axis represents the time that elapsed, and the vertical axis represents the ethanol concentration and the acetic acid concentration in the inoculum culture, with the open area representing ethanol, and the solid area representing acetic acid. FIGS. 2-*a*, 2-*b*, and 2-*c* give the results on *Candida nitrativorans*, *Candida boidinii*, and *Candida hylophila*, respectively. *Candida nitrativorans* shown in FIG. 2-*a*, and *Candida boidinii* shown in FIG. 2-*b* were found to decompose ethanol very quickly, but be slow in decomposing acetic acid. *Candida hylophila* shown in FIG. 2-*c* was found to be capable of decomposing 0.5% (w/v) of acetic acid in about 24 hours in the co-presence of ethanol.

EXAMPLE 1

Method for Eliminating Ethanol by Use of Ethanol-utilizing Microorganism

An acrylic column with an internal diameter of 8 cm and a length of 50 cm was charged with a mixture of 30 g calcium carbonate and 2 liters of peat moss impregnated with an inoculum culture of *Candida nitrativorans* CY 4-1G, which had been selected in Experimental Example 1 as the ethanol-utilizing microorganism, so that the amount of the strain impregnated would be $10^7$ to $10^8$ cells/filter bed (dry weight). This mixture had been adjusted to a water content of 50 to 60%.

The inoculum culture had been obtained by culturing *Candida nitrativorans* CY 4-1G in a liquid medium of the following composition, 21 g Bacto YM Broth (a product of Difco containing 3 g yeast extract, 3 g malt extract, 5 g peptone, and 10 g dextrose) per liter of water, for 24 to 48 hours by the use of a 10-liter jar fermentor.

A gas containing ethanol (2,000 ppm) was generated by blowing air into an aqueous solution of ethanol to make it bubbled. This gas was fed into the acrylic column at a rate of 1 liter/min. The ethanol load capacity was calculated at 120 g/m$^3$/hr. At the exit of the column, the concentration of ethanol in the outlet gas was measured. The measurement of the ethanol concentration in the outlet gas was made by gas chromatography. The conditions for gas chromatography were as follows: a packed column (5% Carbowax 20M/GP 60/80 CarbopackB, 2.6 mm$\phi$×2 m; Supelco) as a column; $N_2$ as a carrier gas, a flow rate of 25 ml/min, temperatures of 100° C. for injection and the column, 200° C. for detection; detection by FID; and a sample amount of 1 ml. When the ethanol removal efficiency reached the 50% level, the test was discontinued.

The results are shown by a curve 3-*a* in FIG. 3. The ethanol concentration in the outlet gas at the exit of the column was always not more than 200 ppm for 180 days (6 months), and the ethanol removal efficiency was 90% or more.

EXAMPLE 2

Method for Eliminating Ethanol with Ethanol-utilizing Microorganism Given Thiamin An acrylic column with an internal diameter of 8 cm and a length of 50 cm was charged with a mixture of 30 g calcium carbonate, 40 g of rice bran containing 1 mg thiamin, and 2 liters of peat moss impregnated with an inoculum culture of Candida nitrativorans CY 4-1G, which had been selected in Experimental Example 1 as the ethanol-utilizing microorganism, so that the amount of the strain impregnated would be $10^7$ to $10^8$ cells/g filter bed (dry weight). This mixture had been adjusted to a water content of 50 to 60%. The inoculum culture had been prepared in the same manner as in Example 1.

A gas containing ethanol (2,000 ppm) was generated by blowing air into an aqueous solution of ethanol to make it bubbled. This gas was fed into the acrylic column at a rate of 1 liter/min. The ethanol load capacity was calculated at 120 g/m³/hr. At the exit of the column, the concentration of ethanol in the outlet gas was measured by gas chromatography in the same manner as in Example 1. When the ethanol removal efficiency reached the 50% level, the test was discontinued.

The results are shown by a curve 3-*b* in FIG. 3. In Example 1, the ethanol removal efficiency tended to decrease, when 180 days passed from the start of operation. In Example 2 in which rice bran was added as a thiamin source, the treating ability expressed as the ethanol removal efficiency of 95% or more was maintained for more than 420 days, as indicated by the curve 3-*b*.

The apparatus according to the present invention is often installed outdoors. Even when this apparatus is installed indoors, a device for controlling the temperature of the room, such as an air conditioner, is minimally provided, and the apparatus of the invention is frequently placed in an environment susceptible to the influence of the atmospheric temperature. Thus, the temperature of the filter bed within the apparatus, usually 20° C. to 38° C. or lower, may rise to 40° C. or higher in the summer season. Furthermore, when the microorganism in the filter bed utilizes ethanol, heat is generated. Thus, in a situation where utilization takes place markedly, too, the temperature of the filter bed may increase to 40° C. or higher. At the filter bed temperature of 40° C. or higher, the growth of the microorganism held in the filter bed becomes slow, and its utilizing ability lowers. In this view, the inventors searched for a microorganism which enables the ethanol eliminating method of the present invention to be carried out, even when the filter bed temperature goes to 40° C. or higher. *Pichia angusta* ATCC 64209, selected in Experimental Example 1 as the microorganism with high ethanol utilizing ability, was deemed to be resistant to high temperatures of 40° C. or higher (Agric. Biol. Chem., 50(4), 827–832, 1986). Thus, the inventors used this *Pichia angusta* ATCC 64209 to perform the ethanol eliminating method, as shown in Example 3 below.

EXAMPLE 3

Method for Eliminating Ethanol with Ethanol-utilizing Microorganism Having Resistance to High Temperatures Two acrylic columns (a and b) with a diameter of 8 cm and a length of 50 cm were charged with mixtures of 30 g calcium carbonate, 40 g of rice bran containing 1 mg thiamin, and 2 liters of peat moss impregnated with an inoculum culture of Candida nitrativorans CY 4-1G, and an inoculum culture of the high-temperature resistant *Pichia angusta* ATCC 64209, respectively, both strains having been selected in Experimental Example 1 as the ethanol-utilizing microorganisms, so that the amount of each strain impregnated would be $10^7$ to $10^8$ cells/g filter bed (dry weight). Each mixture had been adjusted to a water content of 50 to 60%. Each inoculum culture had been prepared in the same manner as in Example 1.

A gas containing ethanol (2,000 ppm) was generated by blowing air into an aqueous solution of ethanol to make it bubbled. This gas was fed into each of the acrylic columns a and b at a flow rate of 1 liter/min. The ethanol load capacity was calculated at 120 g/m³/hr. This test was conducted in a thermostatic chamber at 37° C. At the exit of each column, the concentration of ethanol in the outlet gas was measured by gas chromatography in the same manner as in Example 1. When the ethanol removal efficiency reached the 50% level, the test was discontinued. A thermometer was inserted into the filter bed to measure the temperature of the filter bed during the test.

The results are shown in FIG. 4. A curve 4-*a* shows the results on the column a in which *Candida nitrativorans* CY 4-1G was added to the filter bed. During the test period, the temperature of the filter bed was 37 to 45° C., and the ethanol removal efficiency sharply decreased at the 30th day and later. A curve 4-*b* shows the results on the column b in which *Pichia angusta* ATCC 64209 was added to the filter bed. During the test period, the temperature of the filter bed was 37 to 45° C., but elimination of 95% or more of ethanol was possible under the ethanol load capacity 120 g/m³/hr even at the 90th day.

The results of Example 3 demonstrate that *Pichia angusta* ATCC 64209 permitted the ethanol eliminating method of the present invention to be performed even at the filter bed temperature as high as 40° C. or higher, and provided ethanol removal efficiency of 90% or more for ethanol in the exhaust gas for more than 90 days.

EXAMPLE 4

Method for Eliminating Ethanol by Joint Use of Ethanol-utilizing Microorganism and Microorganism Capable of Utilizing Acetic Acid in the Presence of Ethanol Two acrylic columns (a and b) with a diameter of 8 cm and a length of 50 cm were each charged with a mixture of 30 g calcium carbonate, 40 g of rice bran containing 1 mg thiamin, and 2 liters of peat moss impregnated with an inoculum culture of *Candida nitrativorans* CY 4-1G, which had been selected in Experimental Example 1 as the ethanol-utilizing microorganism, so that the amount of the strain impregnated would be $10^7$ to $10^8$ cells/g filter bed (dry weight). The mixture had been adjusted to a water content of 50 to 60%. The inoculum culture had been prepared in the same manner as in Example 1.

A gas containing ethanol (6,000 ppm) was generated by blowing air into an aqueous solution of ethanol to make it bubbled. This gas was fed into each of the acrylic columns a and b at a flow rate of 1 liter/min. The ethanol load capacity was calculated at 360 g/m³/hr. At the exit of each column, the concentration of ethanol in the outlet gas was measured by gas chromatography in the same manner as in Example 1. For each of the columns, an aqueous solution of 3 g ammonium nitrate and 0.9 g dipotassium hydrogenphosphate was added to the filter bed through the upper end of the column one month after initiation of the test, and once monthly thereafter. To the column b, an inoculum culture of *Candida hylophila* CR 30, which had been selected in Experimental Example 2 as the microorganism capable of utilizing acetic acid in the presence of ethanol, was added in an amount of 20 ml each 17, 47 and 77 days after initiation of the test so that the amount of the strain added would be $10^9$ to $10^{10}$ cells/liter of the filter bed. To the column a, nothing was added. The inoculum culture had been prepared in the same manner as in Example 1. Each test was discontinued when the ethanol removal efficiency reached the 50% level.

The results are shown in FIG. 5. A curve 5-*a* shows the results on the column a without addition of the microorganism capable of utilizing acetic acid in the presence of ethanol. The ethanol removal efficiency sharply decreased at the 20th day and later. A curve 5-*b* shows the results on the column b to which the microorganism capable of utilizing acetic acid in the presence of ethanol was added. 95% or more of ethanol removal efficiency was possible at a high ethanol load capacity of 360 g/m³/hr even on the 90th day in operation.

For the column a, the pH of drainage discharged from the bottom of the column on the 43rd day was measured, and found to be 3.5. When the acetic acid concentration in the drainage was analyzed by HPLC as in Experimental Example 2, 2.5 w/v % of acetic acid was detected. For the column b, the pH of drainage on the 9th, 43rd, 64th and 91st days was measured, and found to be 7.23, 7.59, 7.46 and 7.13, respectively. The acetic acid concentration in the drainage was also analyzed by HPLC, but no acetic acid was detected at any time points.

EXAMPLE 5

Method for Eliminating Ethanol by Use of Ethanol-utilizing Microorganism

An apparatus shown in FIG. 1-$b$ having a filter bed volume of 5 m$^3$ (150 cm×333 cm×100 cm) was charged with 5 m$^3$ of peat moss, 75 kg of calcium carbonate, 100 kg of rice bran, and 100 liters of an inoculum culture of *Candida nitrativorans* CY 4-1G (after mixing, 10$^7$ to 10$^8$ cells/g of dry filter material), which had been selected in Experimental Example 1 as the ethanol-utilizing microorganism, to serve as a filter bed. The inoculum culture had been prepared in the same manner as in Example 1. An exhaust gas containing ethanol in fermentation facilities was diluted with external air to an ethanol concentration of 2,000 ppm, and then passed as a downward flow through the filter bed at the rate of 2.5 m$^3$/min. The ethanol load capacity was calculated at 120 g/m$^3$/hr. At an exhaust vent of the apparatus, the time course of the concentration of ethanol in the outlet gas was measured by gas chromatographic analysis every 96 hours.

An aqueous solution of 15 kg ammonium nitrate and 4.5 kg dipotassium hydrogenphosphate was added to the filter bed through the upper end of the filter bed one month after initiation of the test, and once monthly thereafter. The apparatus was monitored for 1 year since the start of its operation. The ethanol removal efficiency of 90% or more was maintained always stably for one year.

INDUSTRIAL APPLICABILITY

The method of the present invention has an excellent decomposing and eliminating ability, expressed as an ethanol removal efficiency of 90% or higher, for ethanol in an exhaust gas contacted with a microorganism. Even for the decomposition and elimination of ethanol of very high concentration, very high ethanol load capacity such as 120 g/m$^3$/hr or more, the method permits long-term stable elimination. Even for an exhaust gas having a high ethanol load capacity, i.e., 360 g/m$^3$/hr or more, the ethanol removal efficiency is 95% or more. With the conventional method, there is only one report of the ethanol removal efficiency of 90% or more under high ethanol load capacity such as 120 g/m$^3$/hr or more. The method of the present invention, by contrast, has remarkably increased the ethanol removal efficiency, and has permitted long-term decomposition and elimination of an exhaust gas containing a high concentration of ethanol. When an exhaust gas containing 12 kg of ethanol must be decomposed and eliminated in an hour, for example, a filter bed volume of at least 100 m$^3$ is required at a maximum ability which is capable of performing of 120 g/m$^3$/hr according to the earlier technology. An eliminating ability of 360 g/m$^3$/hr according to the present invention, on the other hand, enables the necessary filter bed volume to be decreased to about 33 m$^3$. This has greatly contributed to the down-sizing of a biofilter device, and has widened the range of applications of the biofilter device to ethanol decomposition and elimination. The method of the present invention has a high removing power expressed as the removal efficiency of 95% or more for ethanol in an exhaust gas contacted with the filter bed used in the method. While maintaining this high removing power, the ethanol eliminating method can be performed for a long term when there is a very high concentration of ethanol, and under high ethanol load capacity involving 120 g/m3/hr or more. Furthermore, maintenance of the filter bed containing the microorganism is easy.

Besides, a microorganism capable of utilizing acetic acid in the presence of ethanol is coexisted with an ethanol-utilizing microorganism. This measure makes it possible to control pH in the filter bed, and suppress stress on the microorganism in the filter bed. Consequently, more rapid decomposition and treatment, and ethanol elimination at high performance can be maintained stably for a long term.

In addition, supply of thiamin to the microorganism has permitted long-term decomposition and treatment at a higher speed and with higher ability.

What is claimed is:

1. A method for eliminating ethanol in an exhaust gas which comprises bringing the ethanol in the exhaust gas into contact with the ethanol-utilizing microorganism held in filter bed, thereby decomposing the ethanol, characterized by adding thiamin or a substance containing thiamin to the filter bed in order to promote the decomposition of ethanol.

2. A method for eliminating ethanol in an exhaust gas as claimed in claim 1, wherein the ethanol in the exhaust gas, as well as acetaldehyde, ethyl acetate, and/or acetic acid in the exhaust gas are brought into contact with the ethanol-utilizing microorganism held in filter bed, thereby decomposing the ethanol, acetaldehyde, ethyl acetate, and/or acetic acid.

3. A method for eliminating ethanol in an exhaust gas as claimed in claim 1, further comprising:

bringing the ethanol in the exhaust gas into contact with the ethanol-utilizing microorganism and a microorganism capable of utilizing acetic acid in the presence ethanol held in filter bed, thereby decomposing the ethanol.

4. A method for eliminating ethanol in an exhaust gas as claimed in claim 1, wherein the ethanol-utilizing microorganism is a microorganism selected from the genus Candida, the genus Pichia and/or the genus Hansenula.

5. A method for eliminating ethanol in an exhaust gas as claimed in claim 4, wherein the microorganism capable of utilizing acetic acid in the presence of ethanol is a microorganism selected from the genus Candida.

6. A method for eliminating ethanol in an exhaust gas as claimed in claim 5, wherein the microorganism capable of utilizing acetic acid in the presence of ethanol is *Candida hylophila*.

7. A method for eliminating ethanol in an exhaust gas as claimed in claim 4, wherein the ethanol-utilizing microorganism is selected from *Candida hylophila, Candida nitrativorans, Pichia boidini* and/or *Pichia angusta*.

8. A method for eliminating ethanol in an exhaust gas as claimed in any one of claim 1, wherein the amount of the thiamin or the substance containing thiamin added to the filter bed is 1 µg or more as thiamin per liter of the filter bed.

9. A method for eliminating ethanol in an exhaust gas as claimed in claim 1 further comprising:

performing ethanol removal efficiency of 90% or higher on the condition that ethanol load capacity is 120 g/m$^3$/hr or more.

10. A method for eliminating ethanol in an exhaust gas as claimed in claim 1, wherein the ethanol in the exhaust gas is brought into contact with the ethanol-utilizing microorganism at an ethanol load capacity of 180 g/m$^3$/hr or more.

* * * * *